United States Patent [19]

Marsh et al.

[11] 4,185,073
[45] Jan. 22, 1980

[54] APPARATUS FOR ISO- OR TEREPHTHALIC ACID PRODUCTION IN AND RECOVERY FROM BENZOIC ACID-WATER SOLVENT SYSTEM

[75] Inventors: David R. Marsh, Lisle; Leonard E. Stark, Bristol, both of Ill.

[73] Assignee: Standard Oil Company (Indiana), Chicago, Ill.

[21] Appl. No.: 819,101

[22] Filed: Jul. 26, 1977

Related U.S. Application Data

[62] Division of Ser. No. 708,360, Jul. 26, 1976, Pat. No. 4,081,464.

[51] Int. Cl.$^2$ ............................................. B01J 1/00
[52] U.S. Cl. ............................... 422/111; 260/524 R; 364/500; 422/189; 422/225; 422/235; 562/414
[58] Field of Search .............. 260/524 R; 23/253 A, 23/230 A, 288 R; 364/500; 422/111, 189, 225, 235

[56] References Cited

U.S. PATENT DOCUMENTS

| | | | |
|---|---|---|---|
| 3,150,172 | 9/1964 | Serres, Jr. et al. | 260/524 R |
| 3,254,071 | 5/1966 | Morgan et al. | 23/253 A |
| 3,442,767 | 5/1969 | Hall | 260/524 R X |
| 3,705,787 | 12/1972 | Carli et al. | 23/253 A X |
| 3,839,435 | 10/1974 | Shigeyasu et al. | 260/524 R |
| 3,839,436 | 10/1974 | Longland, Jr. | 260/524 R |
| 3,846,487 | 11/1974 | Shigeyasu et al. | 260/524 R |
| 3,859,344 | 1/1975 | Shigeyasu et al. | 260/524 R |
| 3,887,612 | 6/1975 | Shigeyasu et al. | 260/524 R |

OTHER PUBLICATIONS

Perry, "Chemical Engineers' Handbook-4th Ed.", McGraw-Hill Book Co., 1963; pp. 22-63 to 22-76.

*Primary Examiner*—Arnold Turk
*Attorney, Agent, or Firm*—Fred R. Ahlers; Arthur G. Gilkes; William T. McClain

[57] ABSTRACT

Continuous production of iso- or terephthalic acid in a stirred reaction zone by catalytic air oxidation of m- or p-xylene in the presence of a benzoic acid-water liquid solvent system at constant gauge pressure within the range of 7 to 21 kg/cm$^2$ wherein oxidation temperature within the range of 175° to 235° C. is maintained substantially constant by the novel control thereof by only varying the flow rate of water condensate reflux to the oxidation zone. The invention further pertains to novel means for achieving such temperature control.

Also, the present invention relates to a novel continuous recovery of the phthalic acid product from the fluid effluent of said continuous process by a process wherein crystalline phthalic acid product is separated from essentially water-free benzoic acid mother liquor; the crystalline product is successively washed with liquid benzoic acid and the corresponding xylene; the washed product is dried; and the water removed from said fluid effluent, the benzoic acid and xylene wash liquors, xylene recovered from product drying, and a major proportion of the benzoic acid mother liquor are charged to the oxidation process.

The invention further relates to a novel combination of apparatus for the continuous conduct of said oxidation and recovery processes.

2 Claims, 2 Drawing Figures

APPARATUS FOR ISO- OR TEREPHTHALIC ACID PRODUCTION IN AND RECOVERY FROM BENZOIC ACID-WATER SOLVENT SYSTEM

This is a division, of application Ser. No. 708,360, filed July 26, 1976 and now U.S. Pat. No. 4,081,464.

BACKGROUND OF THE INVENTION

There are disadvantages associated with the commercial exploitation of the continuous preparation of iso- or terephthalic acid by the catalytic air oxidation of m- or p-xylene in the presence of liquid benzoic acid as solvent at operating temperatures in the range of 170° to 274° C. and operating gauge pressures in the range of 21 to 35 kg/cm$^2$ and the requirement to remove by-product water as it is formed according to the disclosure of British Patent No. 1,088,183 published Oct. 25, 1963. The disadvantages are highly discolored to charred product and, under the required conditions for operating pressure and removal of by-product as it forms to use a near zero water content benzoic acid solvent, widely varying oxidation zone temperature which would be unacceptable for commercial operation.

For example, at start-up of such continuous oxidation at a gauge pressure of from 21–35 kg/cm$^2$ and removing by-product water from 5 weight percent down to zero in the benzoic acid solvent the oxidation zone temperature, we found, can increase substantially instantaneously as much as about 110° C. without causing an increase in the operating pressure of 21 to 35 kg/cm$^2$. Such a drastic increase in oxidation zone temperature causes charring of product, intermediates and/or solvent.

We also found that changes in water content of the benzoic acid solvent during continuous operation with by-product water removal after successfully starting without the drastic temperature increase leading to said charring resulted in cycling of oxidation zone temperature above and below a desired constant temperature at a selected constant gauge pressure.

Copending patent application Ser. No. 708,358, filed July 26, 1976, discloses the preparation of iso- or terephthalic acid by the catalytic air oxidation of m- or p-xylene in the presence of liquid benzoic acid solvent which permits commercially feasible temperature control in the range of 175°–235° C., provided the oxidation is conducted in a stirred reaction zone; the solvent consists essentially, on a weight basis of 85 to 97% benzoic acid and 15 to 3% water; and the oxidation zone gauge pressure is constant within the range of 7 to 21 kg/cm$^2$. Said method of iso- or terephthalic acid production is applicable for weight ratios of the benzoic acid-water solvent system to xylene in the range of 2:1 to 8:1. The xylene conversion is substantially complete and high mole percent (% of theory) yields of iso- or terephthalic acid are produced at air ratio which provides 3–10 volume percent oxygen in the exhaust (water and benzoic acid free basis) from the oxidation zone. The catalysis for such oxidation can be provided by manganese, cobalt, or manganese and cobalt as transition metal oxidation catalyst in combination with a source of bromine.

The continuous conduct of such temperature controllable process for preparation of iso- or terephthalic acid comprises simultaneously charging air, xylene and liquid benzoic acid-water solvent system containing the components of catalysis to a stirred tank-type oxidation vessel having a means for withdrawing the fluid oxidation effluent (suspension of crystalline phthalic acid product in the liquid solvent system, means for escape of exhaust (vapors of benzoic acid and water) and the gases, nitrogen, oxygen and oxides of carbon), and means for returning liquid benzoic acid-water condensed from said exhaust in an amount to maintain the 85–97% benzoic acid and 15–3% water solvent system in the oxidation zone. Fluctuations of the oxidation zone temperature are minimized by adjustment of the rate of such benzoic acid-water condensate returned to the oxidation zone. That is, the water content is increased as said temperature increases or decreases as said temperature decreases from a selected operating temperature. The water content of the solvent system in the oxidation zone cannot be permitted to go below 3 weight percent because unacceptably high temperature will occur in the oxidation zone or to go above about 18 weight percent because the xylene oxidation is at a negligible and commercially unacceptable rate.

The present invention provides a novel system for preparing an oxidation charge stock of xylene, solvent system and components of catalysis as well as a novel means for accomplishing control of oxidation at substantially constant temperature without fluctuation of more than ±5° C., preferably ±1° C., therefrom.

STATEMENT OF INVENTION

The present invention comprises in combination the conduct of said continuous air oxidation of m- or p-xylene in the stirred oxidation zone at constant pressure and substantially constant temperature by a novel means for temperature control comprising varying the water content of the liquid reflux to said zone inversely with respect to change required in temperature in said oxidation zone, and the novel recovery of the crystalline iso- or terephthalic acid product suspended in the benzoic acid-water solvent system produced in the oxidation zone. Said novel recovery of iso- or terephthalic acid product comprises the sequential steps of charging said suspension to a water separation zone operated at a temperature and pressure lower than the oxidation zone, but sufficient to maintain the benzoic acid in the liquid phase wherein substantially all of the water is flash evaporated and removed from the water separation zone, separating crystalline iso- or terephthalic acid from the liquid benzoic acid mother liquor; washing the separated crystalline product first with liquid benzoic acid and then with xylene corresponding to said phthalic acid product; recycling a 25 to 90% portion of the benzoic acid mother liquor to the oxidation; distilling the remaining 75–10% portion of benzoic acid mother liquor to remove benzoic acid as a top fraction and leave a fluid residue as bottom fraction; using at least a portion of the benzoic acid top fraction as liquid condensate for said benzoic acid wash of crystalline product; and charging the remaining portion of said benzoic acid top fraction liquid condensate to the oxidation zone together with said benzoic acid and xylene wash liquors together with toluene in an amount at least equivalent to benzoic acid losses.

Temperature control of the catalytic liquid phase air oxidation of m- or p-xylene in the presence of the benzoic acid-water solvent system is sensitive to both pressure of operation and composition of said solvent system. Hence, precise temperature control of such oxidation at substantially constant temperature, e.g., within a range of ±5° C. of a selected temperature, would ordinarily be thought to involve varying both operating pressure and solvent system composition in response to changes of temperature occurring in the oxidation zone. While an integrated control system can be devised to vary operating pressure and solvent system composition in response to fluctuations of operating temperature, such control system would have the disadvantage of subjecting the oxidation reaction vessel to pressure stresses from wide changes in operating pressure, over design of such vessel to operate at the highest pressure to be expected, and the increase potential chance of failure of process control accompanying the varying of two, rather than one, operating conditions.

According to one feature of the present inventive process, precise temperature control of substantially constant operating temperature in the stirred oxidation zone can be attained with no change of operating gauge pressure within the range of 7 to 21 kg/cm$^2$ by only changing the flow rate of the liquid water-benzoic acid reflux, which consists of 90 to 95 weight percent water, returned to the oxidation zone in response to fluctuations of temperature in said zone. Such change of flow rate of the liquid water-benzoic acid condensate (90-95% water) charges the concentration of water in the oxidation zone. Thus by such change of water content in said zone its operating temperature can be controlled. Such unique means for changing one degree of freedom (composition of solvent system in the oxidation zone) does effectively control temperature in a system where two independent degrees of freedom (pressure and solvent system composition) are present. This unique means for control of the temperature sensitive oxidation system means that such oxidation system can be operated at a constant pressure. Also, such unique means for temperature control can automatically provide substantial or complete quenching of the oxidation not only in the event of the occurrence of a temperature increase of more than 5° C. above the selected operating temperature but also in the event of an oxidation temperature upset of the magnitude causing charring of benzoic acid and/or phthalic acid product.

The variation of water flow rate refluxed to the oxidation zone is effective for control of the oxidation zone temperature within the fluctuation range of ±5° C. for an operating temperature within the range of 175°–235° C. and still maintain the water content of solvent system in the oxidation zone at 3 weight percent, but below 15 weight percent for weight ratios of solvent system to xylene in the range of 2:1 to 6:1. Temperature control within a ±1° C. fluctuation range of constant temperature can be achieved for a solvent system consisting essentially of 90–97 weight percent benzoic acid and 10–3 weight percent water and said ratios of solvent system to xylene. Hence, such a solvent system is preferred for the present inventive continuous production and recovery of iso- or terephthalic acid.

Three systems have been devised for control of oxidation reaction temperature by varying the flow rate reflux (90-95% water) to the oxidation zone. Both systems are based on the technical effect of the inverse response to said water content with respect to change of oxidation zone temperature. Such inverse response means that reaction zone temperature can, respectively, be decreased or increased by the increase or decrease of the rate of water returned as liquid reflux to the oxidation zone.

The first system consists of a combination of an external integrating control device; a temperature sensor (e.g., a thermocouple) in the oxidation zone; a partial condenser; a multi-function water-cooled vessel which functions as a total condenser, a water condensate collector and water condensate proportioner having a liquid reflux discharge and a water condensate discharge; and a liquid flow controller. The external integrating control device is connected to the temperature sensor and the liquid flow controller and receives input from the temperature sensor and, in response to its comparison of such input to the selected oxidation zone temperature as a set constant, provides an inverse output response to operate the liquid flow controller. The partial condenser receives exhaust, a mixture of benzoic acid and water vapors, unused portion ($N_2$ and $O_2$) of air feed and oxides of carbon from air and produced by some benzoic acid and xylene burning, and is operated at a constant temperature to produce a benzoic acid-water liquid condensate normal for steady state constant temperature operation. Said normal condensate and uncondensed portions of said exhaust flow to the multi-function water-cooled vessel wherein the remaining water vapor is condensed by a total condenser which has means for collecting the water condensate and proportioning it between water condensate discharge and the liquid reflux discharge. The liquid reflux discharge is connected to the oxidation reaction zone to provide liquid reflux thereto. The liquid flow controller controls the flow of water condensate from said multi-function vessel and, under normal operation, partially open, provides a discharge flow of water condensate from the collector-proportioner equal to the water by-product of the oxidation.

The inverse output response from the external control device closes the liquid flow controller as oxidation zone temperature increases above the set constant temperature, the flow of water condensate discharge is reduced, the water condensate proportioner (weir or dam) in water condensate collector causes more water condensate to be combined with the normal liquid benzoic acid-water reflux to the oxidation zone and lowers its temperature. When the oxidation zone temperature decreases below the selected constant temperature, the inverse output response opens the liquid flow controller to discharge water condensate in excess of the normal flow, and the system returns less water with the liquid benzoic acid-water reflux to the oxidation zone permitting its temperature to increase.

The second system consists of a combination of an external integrating control device, a temperature sensor (e.g., thermocouple) in the oxidation zone; either a combination of a reflux condenser and a heat exchanger heated with steam at a maximum gauge pressure of 7 kg/gm$^2$ and having a steam pressure controller and a steam flow controller, a water-cooled total condenser, a water condensate receiver having a set condensate flow discharge, a pump, and means for transfer of water condensate from its receiver to the oxidation zone; or in place of said combination a reflux heat exchanger which receives exhaust from the oxidation vessel and cools the same by indirect heat exchange with water to generate steam whose exit pressure can be varied by the integrating control device to vary the amount of condensate recycled to the oxidation vessel.

In said combination, the external integrating control device receives input from the temperature sensor and compares said input against the set constant (selected oxidation operating temperature) to provide an inverse output response to the steam pressure and flow controllers. The reflux condenser is an integral part of the oxidation vessel and can be operated at a variable temperature by preheating of the heat exchange fluid supply to the reflux condenser. The minimum temperature of such heat exchange fluid is 0.3°–0.8° C. above the melting point (121.7° C.) of benzoic acid. Preheating of said heat exchange fluid is accomplished by said steam heated heat exchanger through operation of its steam pressure and flow controllers. Normal operation of the integral reflux condenser and heat exchanger is above said minimum temperature and provides liquid benzoic acid-water reflux to the oxidation zone which is normal to steady state oxidation zone temperature. Said inverse output from the external integrating control device increases or decreases steam pressure and flow to the heat exchanger as the oxidation zone temperature decreases or increases, thus decreasing or increasing the operating temperature of the integral reflux condenser which increases or decreases the water content of the liquid reflux to the oxidation zone.

The third system for control of oxidation zone temperature at constant pressure makes use of a direct reflux first partial condenser operated at constant temperature and a variable temperature second condenser. The operating temperature of the first condenser is selected to condense benzoic acid vapor content of the exhaust from the oxidation zone and sufficient water vaporized therein to maintain the selected water content of the benzoic acid-water solvent system. The remainder of the exhaust flows tp the second condenser whose operating temperature is varied inversely with respect to change of temperature in the oxidation zone to provide a variable flow of additional water condensate thereto. The uncondensed exhaust is discharged from the second condenser through a pressure controller set to maintain the selected operating pressure of the oxidation zone.

To accomplish the required change of operating temperature of the second condenser the output of a temperature sensor in the oxidation zone is fed as input to an external integrating control device into which the desired oxidation zone temperature is set as a constant and against which the input corresponding to the temperature of the oxidation zone is compared. From such comparison the control device provides an output response to change the operating temperature of the second condenser inversely with respect to the direction of change from the set temperature. For example, a second condenser cooled by variable temperature water supplied by a steam-water mixer can have its steam valve closed or opened by the integrating controller's output response as the temperature of the oxidation zone increases or decreases from the set constant.

However, any system which functions to vary inversely the amount of water condensate returned to the oxidation zone with an increase or decrease of its temperature is suitable for the temperature control purposes of this invention.

In both of the above systems, the partial condenser, reflux condenser and total condenser are cooled, and the preheating is accomplished by indirect heat exchange.

Operating pressure is set at a pressure control valve in the gas discharge from the multi-function vessel of the first system, in either the gas discharge from the total condenser or condensate receiver of the second system and in the outlet exhaust from the variable temperature condenser of the third system.

The normal operating temperature of the partial condenser or the integral reflux condenser, their operating temperature at steady state conduct of the xylene oxidation generating a constant heat of reaction, can be calculated from their heat removal capacity and the heat they must remove which is the difference between the heat of reaction and the heat removed by their respective total condensers at such steady state condition. For the combination of partial condenser and total condenser, the latter removes the amount of heat required to condense the by-product water. For the combination of integral reflux condenser and total condenser, the latter removes the amount of heat required to condense both the by-product water and recycled water.

Use in the present inventive continuous oxidation of weight ratios of the benzoic acid-water solvent system to m- or p-xylene in the range of 2:1 to 6:1, in addition to providing the built-in reaction quenching also provides a readily flowable fluid oxidation effluent, and substantially water-free effluent easily transferable to the product recovery steps without pumping, and sufficient liquid benzoic acid to retain a substantial amount of aromatic by- and co-products in solution so that the separated, washed and dried phthalic acid product is relatively high, about 99.5% pure.

As before indicated, toluene can be charged to the oxidation zone in an amount to make up benzoic acid losses by burning (total combustion to oxides of carbon and water) and processing to recover product and to recover benzoic acid for reuse. Some benzoic acid will, of course, be lost in its recovery because of a purge from the system of impurity materials whose recycle to oxidation would adversely affect product quality. Such burning and purging losses of benzoic acid, in general, do not exceed 10% of the original benzoic acid in the starting benzoic acid-water solvent solvent. The toluene added to the oxidation zone readily oxidizes to benzoic acid.

The process of this invention can advantageously also provide benzoic acid product for its many known uses. To do so toluene above that required for the 2–6:1.0 benzoic acid-water solvent system can be charged to the oxidation. The additional benzoic acid so produced also functions as solvent for impurity products. Thus an iso- or terephthalic acid product of higher purity will be produced as additional benzoic acid is co-produced as co-product. For the additional production of co-product benzoic acid the concentration of benzoic acid in the solvent system in the oxidation zone should be in the range of 85-97% with the 15-3% water. Also, the same basic means for close temperature control in the oxidation zone is applicable.

The novel recovery of iso- or terephthalic acid is based on novel concept of using to advantage the technical effects of each of the steps of the recovery process. The removal of water from the fluid oxidation effluent, is readily accomplished by flash evaporation of water to a lower temperature and pressure at which benzoic acid remains as a liquid. Such removal of water provides a fluid mixture having a high rate of solids-liquid separation (high drain rate) and a low benzoic acid mother liquor retention by the separated product. Solid-liquid separation, for example, by filtration or centrifugation, leaves a hot solid crystalline product with about five weight percent retained benzoic acid mother liquor. Washing such separated hot crystalline product first with liquid (122°–135° C.) benzoic acid and then with the xylene corresponding to the product again provide high drain rates and low wash liquor retention. Also, the xylene washing, while conducted with hot (122°–135° C.) crystalline product, is conducted below the boiling point of the xylene. The xylene washed product requires little added heat for drying.

Such product recovery system eliminates product crystallization from the oxidation effluent, and water removal from large volumes of mother liquor and vapor scrubbers. The benzoic acid and xylene wash liquors can be used to prepare the feed charge (mixture of solvent system, xylene to be oxidized and system of catalysis).

Distillation of the 10–75% portion of benzoic acid mother liquor not recycled to oxidation for the initial solvent system is conducted to prevent the accumulation of colored and color forming impurities in the fluid oxidation effluent and phthalic acid product otherwise occurring when all of the benzoic acid mother liquor is recycled to feed stock preparation. Such distillation provides at least a part of liquid benzoic acid for product washing. The only benzoic acid makeup is that to replace the small amount in the rejected distillation bottoms fraction. Also such distillation provides a means for recovery of co-product benzoic acid made in addition to its makeup amount.

The minimum liquid benzoic acid to displace the retained benzoic acid mother liquor is about three times said retained mother liquor. But a larger amount of liquid benzoic acid can be used for said first wash because such wash liquor is sent to preparation of the feed stock for the oxidation process. This first washing with liquid benzoic acid also has a high drain rate and leaves a crystalline mass containing about 5 to 10 weight percent benzoic acid.

The xylene wash, m-xylene for isophthalic acid product and p-xylene for terephthalic acid product, is conducted with hot (35° to 100° C.) xylene, well below their boiling points. Since benzoic acid rapidly dissolved in xylene at such temperatures and xylene drains rapidly from the washed crystalline mass, the amount of xylene used in the second wash is not critical. However, efficient process design and operation would indicate using an amount of xylene of at least about three times the retained benzoic acid but a greater amount can be used because the xylene wash liquor is also sent to preparation of feed stock for the oxidation process. The xylene washed crystalline product mass has about 5 to 10 weight percent xylene.

The xylene washed crystalline product mass is still sufficiently hot so that its drying to remove the small amount of retained xylene is readily and rapidly accomplished. Such drying can be accomplished by any known means for contacting the hot, xylene wet crystalline mass. For example, in an enclosed system which is internally heated and recovers xylene vapors. Heating with circulated hot inert gas is preferred. The hot gas containing xylene vapor can be scrubbed after such contact with cool (ambient) temperature liquid xylene to condense xylene vapors to remove them from the circulating gas.

Both iso- and terephthalic acids are substantially insoluble in liquid benzoic acid and xylene at such washing temperatures. Hence, the loss of such phthalic acid products during such washings is negligible.

The combined continuous oxidation and continuous phthalic acid recovery will be further illustrated by a more specific embodiment in the description of the drawings.

DETAILED DESCRIPTION OF DRAWINGS AND EXAMPLE

The drawings will be described in terms of the production and recovery of 1577 kilograms per hour of terephthalic acid (TA) from the air oxidation of p-xylene in the presence of a solution of components of catalysis in the benzoic acid-water solvent system. The corresponding applicable production and recovery of isophthalic acid (IA) from the air oxidation of m-xylene can be readily understood merely by substitutions of m-xylene for p-xylene and IA for TA in said description.

Figure 1:
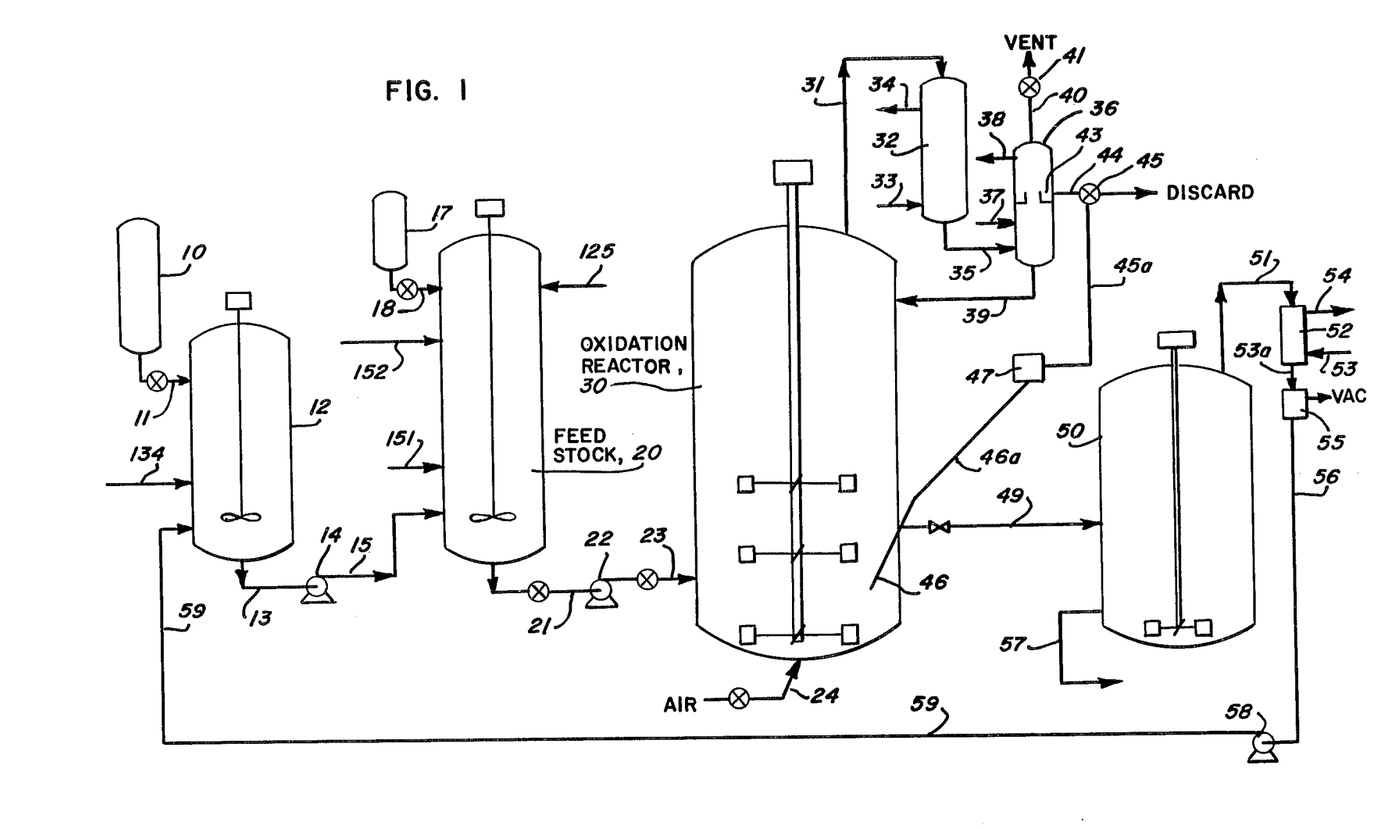
FIG. 1 is both a schematic flow sheet illustration of the present inventive production of iso- or terephthalic acid and an illustration of a preferred combination of apparatus elements including elements to control reaction temperature necessary for the production of said acid product.

The production of TA by the continuous air oxidation of p-xylene is conducted in the combination of apparatus elements shown in FIG. 1.

The oxidation feed stock of p-xylene and solution of components of catalysis (e.g., cobalt and/or manganese acetate tetrahydrates and sodium bromide in the benzoic acid-water solvent system) is prepared in feed stock tank 20 in the following manner. A solution of the components of catalysis in water in catalyst feed tank 10 flows by line 11 into solvent system charge tank 12 and combined therein with recycled water from line 59, benzoic acid mother liquor from line 134 and benzoic acid wash liquid, all later obtained. The amount of water used to dissolve the components of catalysis is not critical to the conduct of the inventive process, because selection of recycled water can be made so that the sum of recycled water and water in solution of components of catalysis will provide the water needed for the selected solvent system.

For the present illustrated production of 1577 kg/hr TA product, there are used 1060 kg/hr of p-xylene and 3180 kg/hr of 94 weight percent benzoic acid-6 weight percent water as the solvent system, a solvent to p-xylene weight ratio of 3:1. Catalysis is provided by 0.2 weight percent manganese and 0.3 weight percent bromine based on the weight of solvent system. Such catalysis in the 3180 kg/hr solvent amounts to 6.36 kg Mn and 9.54 kg bromine. After establishing steady state continuous operation of the oxidation with continuous removal of fluid oxidation effluent, processing such effluent to recover TA product and recycling liquid benzoic acid mother liquor to solvent preparation, the recycled benzoic acid mother liquor (50–90%) will provide 50–90% of the manganese and 50 to 75% of the bromine components of catalysis for oxidation. The 50–10% of manganese not so provided by recycle is then added as a part of the make-up aqueous solution of catalyst components either as dissolved fresh manganous acetate tetrahydrate and/or the manganous salt recovered from processing of nonrecycled benzoic acid mother liquor. The bromine not recycled is, as a practical matter, supplied by fresh sodium bromide, hydrobromic acid or other bromine compounds dissolved in water in the make-up aqueous solution of catalyst components or by bromine recovered from the nonrecycled portion of the benzoic acid mother liquor.

For the purposes of this description, recycle of 50% of the benzoic acid mother liquor is practiced. Thus, 3.18 kg of manganese and 3.34 kg of bromine are recycled. The solution of components of catalysis in feed tank 10 contains an aqueous solution (for feed on an hourly basis) 3.18 kg of manganese and 6.2 kg of bromine from the feed tank.

Said solution of manganese catalyst is fed at the rate of 38.8 kg/hr (solution contains 8.2% Mn metal) via line 11 into stirred solvent system charge tank 12 together with 489 (61% benzoic acid) kg/hr from crystallizer condensate via line 59 and 1346 kg/hr of recycled benzoic acid mother liquor (99.8% benzoic acid) via line 134.

From solvent system charge tank 12 there is taken 1873.8 kg/hr of solution by pump 14 via line 13 and discharged through 15 into stirred feed mix tank 20; 1271 kg/hr benzoic acid wash liquor via line 151; 985 kg/hr p-xylene wash liquor per hour containing 75 kg benzoic acid via line 152; and 150 kg/hr p-xylene from line 125 to provide 4279.8 kg/hr feed mixture for stirred oxidation reactor 30.

Said 4280 kg/hr feed mixture is withdrawn from stirred feed mix tank 20 by pump 22 via open valved line 21 and discharged through open valved feed mixture line 23 into oxidation reactor 30 to enter the lower stirred (axial up-flow) portion of the oxidation zone where the feed mixture is contacted with pressurized air at 2310 nM$^3$/hr from valved air feed line 24 which, as shown, discharges the air just below the bottom impeller. The other stirrer shown provides adequate mixing of the oxidation zone. The bottom stirrer prevents TA solid deposition on the bottom and adjacent wall of oxidation reactor 30.

The operating temperature of the stirred fluid (oxidation zone) in oxidation reactor 30 is in the range of 175°–235° C. and the operating gauge pressure is in the range of 7–21 kg/cm$^2$ set both at pressure control valve 41 and draw-off valve 45. The mixture of water and benzoic acid vapors generated in the reaction zone together with nitrogen, carbon oxides and unreacted oxygen flow from the top of oxidation reactor 30 through reactor vent line 31 to partial condenser 32 where, by indirect heat exchange, a water-benzoic acid mixture (85–90% water, 15–10% benzoic acid) is condensed at a temperature of 125° C. Partial condenser 32 can be so operated by pressurized hot (125° C.) water introduced by inlet 33 and the steam generated leaving by steam discharge line 34. The resulting mixture of condensate, vapors and gases flow from partial condenser 32 through line 35 to total condenser 36 and are cooled by indirect heat exchange with cold water entering by feed line 37 and leaving by hot water discharge line 38. The water vapor not condensed in partial condenser 32 is condensed in total condenser 36 and collected in trap-out ring 43. Uncondensed gas containing 3–10 volume percent oxygen leaves total condenser 36 by gas vent line 40 containing pressure control valve 41. The water-benzoic acid condensate separated from vapors and gases in the bottom of total condenser 36 flows to oxidation reactor 30 via reflux line 39. The water condensate collected by trap-out ring 43 is removed, generally in an amount equal to by-product water produced by the oxidation, through line 44 and draw-off valve 45. Any water not so removed overflows trap-out ring and flows via reflux line 39 to oxidation reactor 30.

Temperature control in the stirred oxidation zone is achieved with the foregoing combination of oxidation reactor 30, partial condenser 32 and total condenser 36 by means of controller 47 where operating temperature is set at a fixed temperature, in this case 205° C. When the input from lead 46a of temperature sensor 46 (e.g., thermocouple) inserted in the stirred reaction zone indicates to controller 47 that the reaction temperature is above or below 205° C., the output from controller 47 closes (temperature increase) or opens (temperature decrease) draw-off valve 45 to permit removal of more or less water condensate collected by trap-out ring 43. This is done while keeping the reactor pressure constant.

In a preferred modification of the above system the vapors are first partially condensed at 176°–177° C. and then sent to the second condensed at 150° C. and finally condensed to provide an outlet temperature of 48°–50° C. Thus useful steam can be generated by the first two condensers.

The fluid oxidation reaction effluent flows from the stirred oxidation zone in oxidation reactor 30 through valved effluent time 49 to stirred receiving vessel 50 operated at a reduced pressure of 400–420 mm Hg by a source of vacuum (not shown) applied to condensate receiver 55. By such operation, the water component of the solvent system is flash evaporated, the temperature of the water-free effluent remains above 122° C. so benzoic acid does not crystallize. The vaporized water and benzoic acid flow from the top of stirred receiving vessel through vapor transfer line 51 to condenser 52 cooled by indirect heat exchange by water entering by inlet 53 and leaving by exit 54. The water and benzoic acid condensate flows through line 53a to receiver 55 from whence it is taken by pump 58 at 489 kg/hr by line 56 and discharged through line 59 to solvent system charge tank 12.

Figure 2:
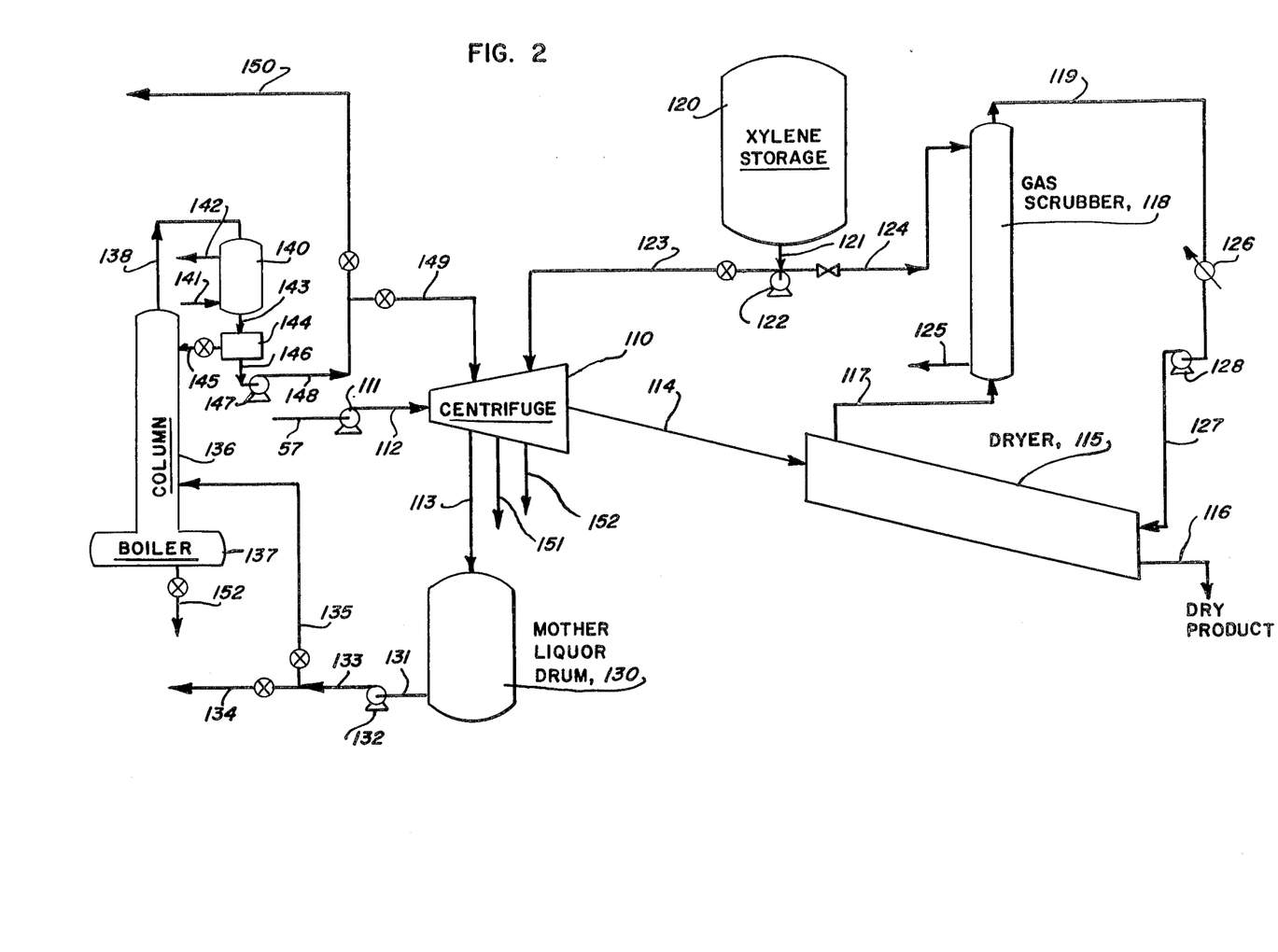
FIG. 2 is both a schematic illustration of a preferred technique for recovery of iso- or terephthalic acid product from the effluent from present inventive production of said acid and an illustration of a preferred combination of apparatus elements for recovery of such product.

The fluid suspension of crystalline TA in liquid benzoic acid mother liquor (solution of components of catalysis and intermediate and co-oxidation products) is taken from stirred receiving vessel 50 via slurry transfer line 57 to TA recovery shown in FIG. 2 discussed below.

Such fluid suspension of impure TA in the liquid benzoic acid mother liquor is taken from slurry transfer line 57 by pump 111 and discharged through slurry feed line 112 into a centrifuge or filter 110 to effect solid-liquid separation of 4268 kg/hr slurry of 1577 kg TA in 2691 kg/hr benzoic acid mother liquor. The separated crystalline TA contains about 5 weight percent benzoic acid mother liquor, is successively washed in centrifuge 110 with 1271 kg/hr recovered liquid benzoic acid at 145° C. from valved conduit 149 and with 985 kg/hr of p-xylene at washing temperature of 50°–100° C. (well below the boiling point (138.5° C.) of p-xylene) from line 123. The benzoic acid wash liquor, about 1271 kg/hr, contains the benzoic acid mother liquor left on TA centrifuge cake and is charged via line 151 (by pumping not shown) to feed mix tank 20. The p-xylene wash liquor, about 985 kg/hr containing 75 kg benzoic acid, is also charged (by pumping not shown) via line 152 to feed mix tank 20.

Twice-washed TA is charged via solid feed line 114 (e.g., screw conveyor) from centrifuge 110 to a dryer, such as rotary tube dryer 115, and discharged therefrom as dry product through product discharge 116. Such drying of TA product can be accomplished by circulating hot (140°–150°) inert gas ($N_2$ or $CO_2$) from gas line 127 heated by heat exchanger 126 and pumped by blower 128 into the dryer. The dryer vaporizes p-xylene from TA feed and the gas-vapor mixture exits therefrom through line 117 into gas scrubber 118 wherein p-xylene vapor is scrubbed and condensed with ambient temperature p-xylene, about 75 kg/hr, introduced into gas scrubber 118 by feed line 124. The p-xylene scrubber liquor at 150 kg/hr flows in line 125 from gas scrubber 118 to feed mix tank 20.

Xylene storage tank 120 is provided to supply via line 121 and pump 122 the p-xylene (985 kg/hr) for TA washing in centrifuge 110 via valved wash line 123 and p-xylene (75 kg/hr) via valved line 124 to gas scrubber 118.

Returning again to solid-liquid separation of the slurry of TA in benzoic acid mother liquor in slurry feed line 112, such separation and subsequent washings of TA first with liquid benzoic acid and then with p-xylene can be also conducted in a vacuum filter. The benzoic acid mother liquor from such solid-liquid separation in line 113 is collected in mother liquor drum 130 from which it is taken through line 131 by pump 132 discharging into line 133. Such benzoic acid mother liquor is split into a recycle portion flowing in valved recycle line 134 in amounts in range of 50–90%, (in this case 50%), or 1346 kg/hr, to solvent system charge tank 12. The remaining 50–10% portion (in this case 50%) or about 1346 kg/hr, containing about 99.8 weight percent benzoic acid and 0.2 weight percent comprising mainly metal components of catalysis but also aromatic intermediate and co-oxidation products, flows in valved line 135 to stripping column 136. Benzoic acid is vaporized in said column 136 by vapors generated in reboiler 137. Materials boiling higher than benzoic acid are withdrawn from reboiler 137 by valved line 152 for discard or, preferably, for recovery of catalyst metals. Such high boiler liquid in this case amounts to about 20 kg/hr and contains benzoic acid, metal catalyst components as benzoates as well as oxygenated intermediates (p-toluic acid and 4-carboxybenzaldehyde) and undesirable aromatic co-products, mainly fluorescing compounds.

Benzoic acid vapors removed from the mother liquor and fed to stripping column 136 flow from the top thereof through line 138. Benzoic acid condenser 140 is operated to provide benzoic acid condensate at a temperature of 145° C. by indirect heat exchange with an appropriate fluid fed to condenser 140 by line 140 and discharged through line 142. Benzoic acid condensate flows from condenser 140 through line 143 to condensate receiver 144 from which part of the condensate flows through valved conduit 145 as reflux liquid to stripping column 136, and the remaining benzoic acid condensate is taken by pump 147 from line 147 and discharged through line 148 to supply liquid benzoic acid via valved line 149 as wash for separated TA and through valved line 150 as recovered benzoic acid supply to solvent system charge tank 12.

The liquid high boiling material withdrawn from reboiler 137 via valved line 152 can be extracted with water liquid at 100°–125° C. to recover about 95% of the manganese and bromine component of catalysis. Such extraction provides an aqueous solution containing manganese benzoate, ionic bromine, benzoic acid and p-toluic acid. The extract solution can be charged to solvent system charge tank 12. By the use of such catalyst metal recovery and the aforementioned recycle of a 50–90% portion of benzoic acid mother liquor, the make-up manganese supplied by catalyst feed tank is only about 5% of total manganese in the system catalysis needed in oxidation reactor 30.

By the conduct of the present inventive continuous oxidation and recovery processes as described above, there can be obtained a recovered, dry terephthalic acid product amounting to a 95–97 mole percent yield and having the typical purity and color properties indicated below.

| Impurity Compounds | |
| --- | --- |
| p-Toluic acid, ppm | 57 |
| 4-Carboxybenzaldehyde, ppm | 1300 |
| Other aromatic co-products, wt. % | 0.1 |
| Optical Density (340 nm light) | 0.6 |
| b-Value | 1.3 |

The effect of benzoic acid mother liquor recycle to oxidation on unwashed recovered terephthalic acid product is indicated in the following examples.

EXAMPLE 2

Comparable p-xylene oxidations are conducted at a temperature of 205° C. and a gauge pressure of 19 kg/cm$^2$ using a weight ratio of solvent system (90% benzoic acid - 10% water) to p-xylene of 3.3:1.0 and 0.013% cobalt, 0.09% manganese and 0.18% bromine, all weight percent of the elements on the solvent system. The oxidation process is, however, varied with respect to recycle of benzoic acid mother liquor to determine the effect thereof at two different levels. Said mother liquor is the liquid obtained after flash evaporation of water from the fluid reaction effluent and separation of suspended crystalline terephthalic acid product. The mole percent (% theory) yield of terephthalic acid recovered are given for 0%, 74% and 40% recycle of mother liquor. The 74% mother liquor recycle is made a phase B of the oxidation after conducting the first oxidation (phase A) with no mother liquor recycle. The 40% mother liquor recycle (phase C) is carried out with mother liquor from such 74% recycle.

The yields, 4-CBA content, optical density at 340 nm and yellowness b-value are shown below for unwashed filter cake.

TABLE II

| TREND EFFECTS FROM MOTHER LIQUOR RECYCLE | | | |
| --- | --- | --- | --- |
| | Phase A | Phase B | Phase C |
| Mother liquor recycle, wt % | 0 | 74 | 40 |
| Terephthalic acid yield, mole % | 97 | 93 | 92 |
| 4-CBA, wt % | 0.29 | 0.69 | 1.1 |
| Optical density, 340 nm | 0.95 | 1.7 | 1.1 |
| Yellowness b-value | 4.1 | 3.0 | 2.1 |

Although recycle of benzoic acid mother liquor did cause a slight decrease in product yield reflected in a higher 4-CBA content of recovered product and an increase in optical density, such recycle did cause a lowering of the yellowness b-value. After conducting Phases B and C it was found that catalyst components had been lost from mother liquor upon each separation of terephthalic acid product. By addition of catalyst components after each of such separation to keep their concentration constant throughout, the yield loss and increase in 4-CBA and optical density value could be substantially avoided. However, it is surprising that as a result of such recycles, there was a desirable decrease in the yellowness b-value.

The following six examples of p-xylene oxidation in TABLE III illustrate the use of the before-mentioned third system for control of oxidation zone temperature. The operation of the second condenser is indicated by its discharge temperature. In each oxidation the solvent system is 90% benzoic acid-10% water. The rate of p-xylene charged in each of Examples 3–5 is the same but the rate in each of Examples 6–8 is 1.5 times that of the first three examples. The relative rate of reaction, hence heat release, at the same operating pressure is qualitatively indicated reaction temperature and by the rate of p-xylene charged. The oxygen content of the exhaust (higher oxygen contents are associated with greater air input) indicates oxygen concentration in the solvent. The low discharge temperatures are associated with oxidation temperature above the selected operating temperature. The high discharge temperatures are associated with the oxidation temperature below the selected operating temperature.

TABLE III

| Example No. | 3 | 4 | 5 | 6 | 7 | 8 |
|---|---|---|---|---|---|---|
| Pressure, kg/cm$^2$ | 17.6 | 17.2 | 20.4 | 20.4 | 19.7 | 19.7 |
| Oxidation Zone Temperature: | 207 | 205 | 215 | 215 | 221 | 221 |
| Deviation: above selected, °C. | 3 | 1 | 2 | 7 | 1 | 1 |
| below selected, °C. | 5 | 2 | 1 | 1 | 6 | 6 |
| Discharge Temperature: | | | | | | |
| low, °C. | 84 | 54 | 54 | 80 | 54 | 54 |
| high, °C. | 108 | 112 | 112 | 117 | 107 | 111 |
| Average O$_2$ in Exhaust, vol. % | 7 | 11.5 | 10.5 | 6.5 | 9.5 | 10.5 |

The foregoing data indicates the closeness of control of oxidation temperature provided by the third system.

For production of fiber and filament from the polyester derived first by direct esterification of terephthalic acid with ethylene glycol in a 1.0:1.1–1.6 mole ratio followed by polycondensation to the desired molecular weight polyester, others have reported that an acceptable terephthalic acid reactant can have a 4-CBA content of from 300 up to 1000 ppm provided such reactant has an optical density of less than 1.0 and a b-value (color of solid reactant exposed to incandescent light) of from −2 up to +2, wherein according to an industry standard color rating the negative value is a measure of blueness and the positive value is a measure of yellowness.

The successive washing of the water-free oxidation product of this invention first with liquid benzoic acid and then with xylene according to the present inventive process can lower the optical density by a factor of from 0.5 to 0.3 of the initial unwashed value while removing benzoic acid contributed by reaction solvent and wash solvent and by-product p-toluic acid. But, such washing technique does not lower the 4-CBA content to said 300 to 1000 ppm range.

However, the carboxybenzaldehyde (4-CBA in TA and 3-CBA in IA) can be substantially lowered in the unwashed, water-free oxidation product by a factor of from 0.5 to 0.2 by the use of secondary oxidation prior to the flash evaporation of water from the effluent of the primary oxidation of p- or m-xylene. For example, when the oxidation is conducted as described with respect to FIG. 1 and the water-free oxidation effluent in transfer line 59 has a carboxybenzaldehyde content of from 3000 to 1300 ppm, the insertion of a secondary oxidation step between the primary oxidation conducted in oxidation vessel 30 and low pressure receiving vessel 50 can lower the carboxybenzaldehyde content of the effluent to 1000 to 260 ppm.

Such secondary oxidation is conducted continuously by charging primary oxidation effluent from transfer line 49 to a second stirred-tank oxidation vessel and introducing only air into said second oxidation vessel. The residence time in the secondary oxidation vessel can be short, e.g., from 10 to 40 minutes. Since the concentration of oxidizable materials (e.g. carboxybenzaldehyde and toluic acid) in the effluent from primary oxidation are relatively low and their oxidation, although rapid, gives off relatively little heat, the secondary oxidation can be conducted at the same pressure as the primary oxidation or even from 0.5 to 5 kg/cm$^2$ lower without the use of the foregoing means for temperature control used for the primary oxidation. Part, up to 50%, of the removal of water from the benzoic acid-water solvent system can be accomplished during the secondary oxidation. The introduction of air into the liquid in the secondary oxidation should provide at least 2 and even as much as 10 volume percent oxygen in the exhaust therefrom. The exhaust from secondary oxidation need only be cooled to condense any benzoic acid vaporized therein and return liquid benzoic acid thereto.

The fluid effluent from such secondary oxidation then flows through the flow control valve at the inlet to low pressure receiving vessel 50 and into said vessel for evaporation and removal of the water content of the secondary oxidation effluent.

The improved product (washed and dried) from a 30 to 40 minute residence secondary oxidation of the primary fluid oxidation effluent of Example 1 may be expected to have a 4-CBA content in the range of 300 to 500, an optical density of from 0.2 to 0.4 and a b-value of from 0.3 to 0.8. The same 30 to 40 minute secondary oxidation of fluid oxidation effluent of Phase A of Example 2 will improve the washed and dried terephthalic acid product to an optical density (340 nm) of from 0.3–0.6, 4-CBA content of from 300 to 900 ppm and a b-value of from 0.5 to 1.5.

The invention claimed is:

1. For the continuous production of iso- or terephthalic acid in a solvent system consisting essentially of 90 to 97 weight percent benzoic acid and 10 to 3 weight percent water by the catalytic air oxidation of m- or p-xylene at a constant gauge pressure of from 7 up to 21 kg/cm$^2$ and at a controlled, selected temperature within the range from 175° C. up to 235° C. wherein heat of reaction is removed by vaporization of water and benzoic acid from the solvent system and control of the selected temperature is effected by varying the rate at which water condensate is returned to the solvent system to a rate inverse to the rate of change from the selected reaction temperature and in an amount such that the water concentration in the solvent system does not go below the 3 percent nor above the 10 percent in the solvent system; the combination of elements of apparatus comprising a stirred-tank-type oxidation vessel having a stirred zone comprising the portion of the vessel's liquid contents kept in flow by the vessel's stirring elements amd said vessel being closed at its top and bottom and further having an air inlet into the bottom of the vessel below its stirred zone, a liquid feedstock inlet into a lower portion of the stirred zone, a liquid inlet into an upper portion of the stirred zone, means for sensing the temperature of the fluid in the lower portion of the stirred zone between the feedstock inlet and the air inlet and providing an output corresponding to the selected temperature, and an exhaust outlet in its top for discharge of gaseous mixture containing vapors of benzoic acid and water from said vessel; a reflux condenser connected with said exhaust outlet to receive said exhaust and condense benzoic acid and partially condense water as liquid reflux recycled to the stirred zone through said exhaust outlet and to discharge a first uncondensed portion of such gaseous exhaust containing water vapor; means for condensing an amount of water from said uncondensed portion of such gaseous exhaust at a rate varying inversely to the rate of change of temperature of the fluid in said stirred zone indicated by the output from said temperature sensor; an external integrating control means capable of having set therein a constant corresponding to the temperature to be maintained in the oxidation zone, receiving as input thereto the output of said temperature sensor in the oxidation vessel, comparing said input to said constant, and providing an output inverse to said comparison; means for transfer of the output of the temperature sensor to the input of the integrating means; means for transfer of said inverse output to the variable water condenser to increase or decrease its operating temperature as the temperature of the stirred zone decreases or increases thereby decreasing or increasing the rate at which water is condensed; means for transfer of said water condensate to the liquid inlet into the upper portion of the vessel, and means for transfer of the second uncondensed portion of the exhaust through a pressure controller maintaining the system at constant pressure.

2. The combination of apparatus elements for continuous production of iso- or terephthalic acid in and recovery from the solvent system consisting essentially of 90 to 97 percent benzoic acid and 10 to 3 percent water on a weight basis by the constant pressure and temperature controlled catalytic air oxidation of m- or p-xylene, which combination comprises a stirred-tank type oxidation vessel having a stirred zone comprising the portion of the vessel's liquid contents kept in flow by the vessel's stirring elements and said vessel being closed at its top and bottom and further having an air inlet in the bottom of the vessel extending into the bottom of the stirred zone, an inlet into a lower portion of the stirred zone for charging thereto a liquid feedstock comprising said xylene and said solvent system containing dissolved components of catalysis, an inlet into an upper portion of the oxidation vessel; means for sensing the temperature in the stirred zone between the inlets for liquid feedstock and air and providing an output corresponding to the sensed temperature, an exhaust outlet in the top of the oxidation vessel, and a fluid overflow outlet in the upper portion of the stirred zone; a partial condenser and a unitary total condenser—condensate receiver; means for transfer of exhaust from said exhaust outlet into the partial condenser; means for transfer of condensate and uncondensed exhaust from the partial condenser into the unitary total condenser—condensate receiver; said unitary total condenser—condensate receiver including a top, a bottom, and upper lower and central portions, and having at the top thereof a pressure controlled gas vent, a condensing section in the upper portion thereof, an internal combination of condensate trap and overflow in the central portion thereof, a variable condensate discard outlet from said condensate trap, and at the bottom thereof a condensate receiver having a condensate outlet in its bottom portion; means for transfer of condensate from the outlet of the condensate receiver to the inlet in the upper portion of the oxidation vessel; an external integrating means for receiving as input the output of the temperature sensor, comparing a set constant corresponding to the temperature to be maintained in the stirred zone of the oxidation vessel and providing an output inverse to said comparison; means for transfer of the output of the temperature sensor to the input of the integrating means; means for transfer of said inverse output to the variable condensate discard outlet to decrease or increase condensate discard as the temperature in the stirred zone increases or decreases thereby increasing and decreasing the flow of condensate to the stirred zone to counter-act its temperature change; a stirred flash evaporation vessel closed at the top and bottom thereof having condenser; stirred suspension zone comprising the portion of the vessel's fluid contents kept in flow by the vessel's stirring elements to maintain solids in suspension and further having a fluid flow controlled inlet into an upper portion of the stirred suspension zone, a vapor outlet in the top of the evaporation vessel and a fluid discharge outlet from a lower portion of the stirred suspension zone; a vapor condenser, a vapor condensate receiver and a pump; means for transferring vapor from the vapor outlet at the top of the flash evaporation vessel to the inlet of the vapor condenser, means for transferring condensate to the condensate receiver and thence to the suction of the pump and means for transferring condensate from the discharge of the pump to the feedstock inlet of the stirred oxidation vessel; means for transferring fluid suspension of solids from the overflow outlet of the stirred zone of the oxidation vessel to the fluid flow controlled inlet to the stirred suspension zone of the flash evaporation vessel; a solid-liquid separating means having an inlet for fluid suspension of solids in the benzoic acid-water solvent system mother liquor, an outlet for said mother liquor, an inlet for benzoic acid wash liquid, an outlet for the wash liquor, and a discharge for washed solids; means for pumping fluid suspension fom the fluid outlet of the flash evaporation vessel to said solid-liquid separating means; a mother liquor pump; means for transfer of separated mother liquor from the mother liquor outlet of the solid-liquid separating means to the suction of the mother liquor pump; a mother liquor still for separating benzoic acid from higher boiling materials, said still having a feed inlet, a top vapor outlet a bottom discharge in its reboiler, a benzoic acid vapor condenser, and a benzoic acid condensate receiver; means for varying fluid flow transfer of mother liquor from the discharge of its pump to both the feedstock inlet of the oxidation vessel and the inlet of said still; means including a pump and fluid flow control for transferring liquid benzoic acid from the benzoic acid condensate receiver to both the feedstock inlet to the oxidation vessel and the wash liquid inlet of said solid-liquid separating means; means for transferring wash liquor therefrom to the feedstock inlet of the oxidation vessel; means for supplying liquid xylene to the wash liquid inlet of the solid-liquid separator; means for transfer of xylene wash to the feedstock inlet of the oxidation vessel; a dryer for twice washed iso- or terephthalic acid product having circulating inert gas to remove vaporized xylene, an inlet for said washed product, a discharge for dried product, a hot gas inlet, and a vent outlet for the mixture of inert gas and xylene vapor; a closed gas scrubber having a gas vent at the top thereof, an inlet at the bottom thereof, a liquid inlet at an upper portion thereof and a liquid outlet in a lower portion thereof; means for transfer of liquid xylene to said upper liquid inlet and from the lower liquid outlet to the feedstock inlet of the oxidation vessel; means for transfer of xylene vapor and inert gas from the vent outlet of the dryer to the bottom inlet of the scrubber; and means for transferring gas from the gas vent of the scrubber through means for indirect heating of the gas and back to the hot gas inlet of said dryer.

* * * * *

UNITED STATES PATENT OFFICE
CERTIFICATE OF CORRECTION

Patent No. 4,185,073    Dated Jan. 22, 1980

Inventor(s) David R. Marsh and Leonard E. Stark

It is certified that error appears in the above-identified patent and that said Letters Patent are hereby corrected as shown below:

The Patent Reads:

| Col. | Line | | | | |
|---|---|---|---|---|---|
| 3 | 10 | "increase" | and should read | --increased-- |
| 3 | 23 | "charges" | " | " | " | --changes-- |
| 4 | 25 | "refllux" | " | " | " | --reflux-- |
| 4 | 52 | "$kg/gm^2$" | " | " | " | --$kg/cm^2$-- |
| 5 | 30 | "tp" | " | " | " | --to-- |
| 9 | 22 | "through 15" | " | " | " | --through line 15-- |
| 10 | 21 | "second condensed" | " | " | --second condensor-- |
| 10 | 27 | "time" | " | " | --line-- |
| 11 | 51 | "line 140" | " | " | --141-- |

UNITED STATES PATENT OFFICE
CERTIFICATE OF CORRECTION

Patent No. 4,185,073    Dated Jan. 22, 1980

Inventor(s) David R. Marsh and Leonard E. Stark

It is certified that error appears in the above-identified patent and that said Letters Patent are hereby corrected as shown below:

The Patent Reads:

| Col. | Line | | | | |
|------|------|---|---|---|---|
| 11 | 57 | "line 147" | and should read | --line 146-- |
| 15 | 6 | "amd" | " " " | --and-- |
| 15 | 10 | "stirred zone" | " " | --vessel-- |
| 16 | 28 | "having condensor; stirred" | " | --having a stirred-- |
| 16 | 4 | "upper lower" | " " | --upper, lower-- |
| 16 | 52 | "fom" | " " | --from-- |
| 16 | 59 | "outlet a" | " " | --outlet, a-- |

Signed and Sealed this

Sixteenth Day of September 1980

[SEAL]

Attest:

Attesting Officer

SIDNEY A. DIAMOND

Commissioner of Patents and Trademarks